United States Patent [19]

Turnbull

[11] Patent Number: 5,769,071
[45] Date of Patent: Jun. 23, 1998

[54] HUMIDIFIER SYSTEMS

[75] Inventor: Christopher Stratton Turnbull, Hythe, England

[73] Assignee: Smiths Industries PLC, London, England

[21] Appl. No.: 787,820

[22] Filed: Jan. 23, 1997

Related U.S. Application Data

[63] Continuation of Ser. No. 588,419, Jan. 18, 1996, abandoned.

[30] Foreign Application Priority Data

Feb. 16, 1995 [GB] United Kingdom .................... 9503012

[51] Int. Cl.⁶ ............................................. A61M 15/00
[52] U.S. Cl. ............................... 128/203.12; 128/203.17; 128/205.23; 128/204.13
[58] Field of Search .................... 128/203.12, 203.16, 128/203.17, 203.26, 204.13, 205.18, 204.18, 205.11, 205.23

[56] References Cited

U.S. PATENT DOCUMENTS

| | | | |
|---|---|---|---|
| 4,010,748 | 3/1977 | Dobritz ............................... | 128/203.27 |
| 4,318,398 | 3/1982 | Oetjen et al. ....................... | 128/204.13 |
| 4,708,831 | 11/1987 | Elsworth et al. ................... | 128/203.17 |
| 4,821,709 | 4/1989 | Jensen ................................. | 128/205.11 |
| 4,829,998 | 5/1989 | Jackson .............................. | 128/203.17 |
| 5,148,801 | 9/1992 | Douwens et al. .................. | 128/203.16 |
| 5,284,160 | 2/1994 | Dryden .............................. | 128/203.12 |
| 5,349,946 | 9/1994 | McComb ........................... | 128/203.17 |
| 5,429,123 | 7/1995 | Shaffer et al. ..................... | 128/204.23 |
| 5,546,931 | 8/1996 | Rusz .................................. | 128/203.12 |

FOREIGN PATENT DOCUMENTS

| | | | |
|---|---|---|---|
| 0 190 080 | 8/1986 | European Pat. Off. ....... | A61H 15/00 |
| 1294808 | 11/1972 | United Kingdom .......... | A61M 16/00 |
| 1448473 | 9/1976 | United Kingdom .......... | A61M 16/00 |
| 1490974 | 11/1977 | United Kingdom .......... | A61M 15/00 |
| 2176405 | 12/1986 | United Kingdom .......... | A61M 16/16 |
| 2192136 | 1/1988 | United Kingdom .......... | A61M 16/16 |

*Primary Examiner*—Mickey Yu
*Assistant Examiner*—V. Srivastava
*Attorney, Agent, or Firm*—Pollock, Vande Sande & Priddy

[57] ABSTRACT

A medical humidifier system for supplying humdified gas to a patient has a heat and moisture exchange device supplied with water from a pump, which is heated by a heater. A tracheal tube is connected to receive the humidified gas via tubing and a connector. The connector is mated with the machine end of the tracheal tube and includes a humidity sensor the output of which is connected to control humidification by controlling the speed of the pump and/or the temperature of the heater.

6 Claims, 1 Drawing Sheet

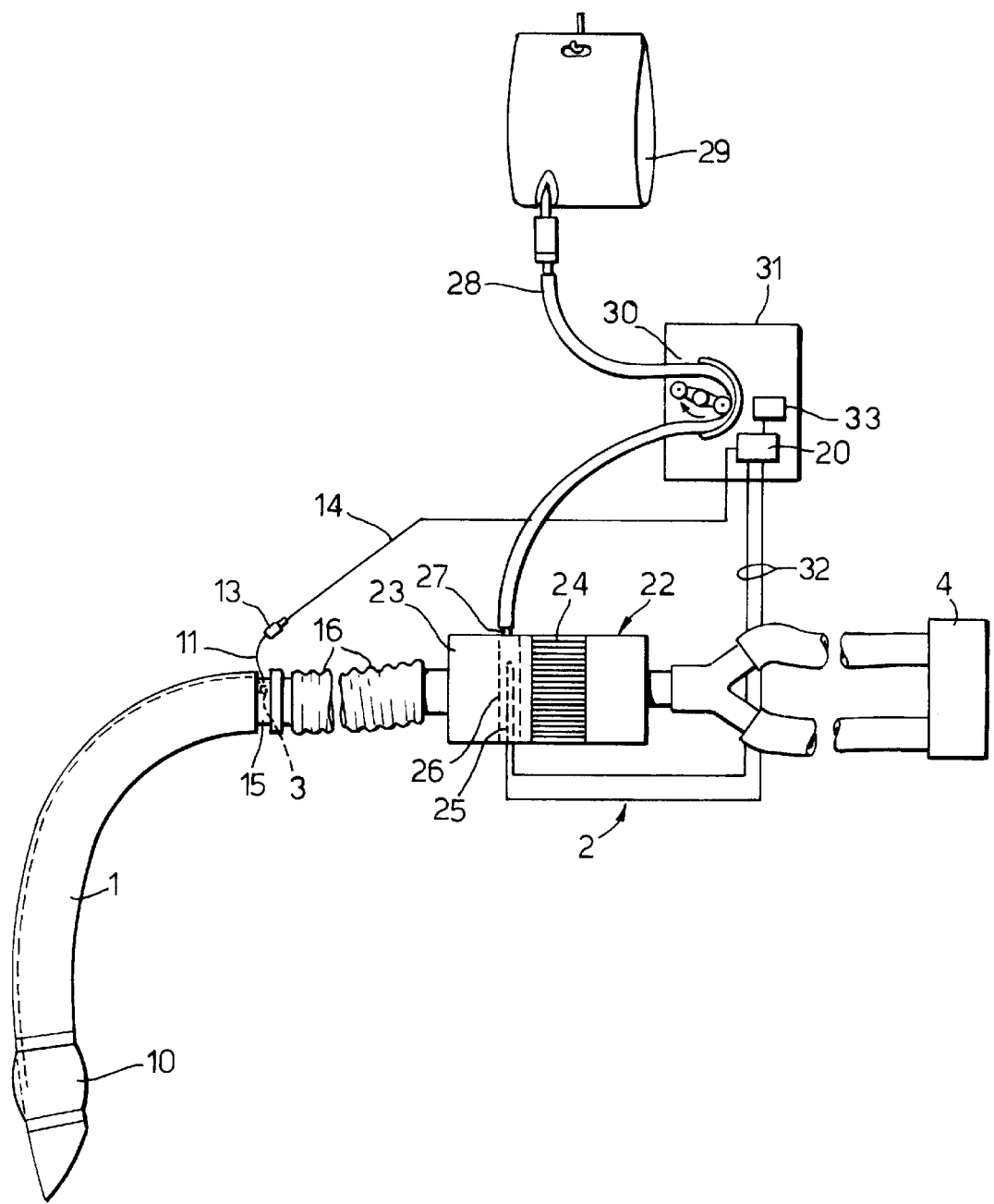

HUMIDIFIER SYSTEMS

This application is a continuation of U.S. patent application Ser. No. 08/588,419, filed Jan. 18, 1996, now abandoned.

BACKGROUND OF THE INVENTION

This invention relates to humidifier systems for use in a medical environment.

Humidifier systems comprising a humidifier and a tracheal tube or mask are used to increase the humidity of gas supplied to a patient.

Examples of such systems are described in WO 91/19527 and 9522267. The humidifier usually incorporates a heater arranged to vaporize liquid water. The heater may be self-regulating, or a separate temperature sensor may be provided to indicate the temperature of gas supplied to the patient. The humidity can be varied by altering the rate of water flow to the humidifier and this can be controlled in response to sensed temperature. This does not, however, provide a very accurate control of humidity.

BRIEF SUMMARY OF THE INVENTION

It is an object of the present invention to provide a system that can be used to provide improved humidity control of a gas supplied to a patient.

According to the present invention there is provided a humidifier system comprising a humidifier, gas supply means connected to the humidifier to supply humidified gas to the patient, and humidity sensor means connected in the gas supply means to control the humidity of gas supplied to the patient.

The gas supply means may include a tube and a connector connected with the tube, the humidity sensor being mounted in the connector. The tube may be a tracheal tube, the gas supply means including tubing connected between the machine end of the tracheal tube and the humidifier, and the connector being connected between the tracheal tube and the tubing. The output of the humidity sensor is preferably connected to the humidifier to control humidification of the gas. The humidifier may include a heat and moisture exchange device, a supply of water to the exchange device and a heater for heating the water supplied to the exchange device. The humidifier may include a water pump, the output of the humidity sensor being connected to control the speed of the pump. The output of the humidity sensor may be connected to control the temperature of the heater.

A humidifier system according to the present invention will now be described, by way of example, with reference to the accompanying drawing.

BRIEF DESCRIPTION OF THE DRAWING

The drawing shows the humidifier system schematically.

DETAILED DESCRIPTION OF THE PREFERRED EMBODIMENT

The system comprises a tracheal tube 1, or other breathing device, connected to humidifier apparatus 2 controlled by a humidity sensor 3. The system is connected to ventilator apparatus 4.

The tracheal tube 1 is of conventional construction, having cuff 10 around its patient end, which seals with the trachea when inflated. At its machine or proximal end, the tube 1 is connected to a connector 15. The connector 15 includes a humidity sensor 3 exposed to gas flowing along the interior of the connector and hence along the tube. A wire 11 extends from the sensor 3 and is connected via a coupling 13 to a cable 14 extending to a control unit 20 of the humidifier apparatus 2. The sensor 3 could be mounted at various other locations such as, in the tube 1 itself, for example at its patient end, or in flexible tubing 16 connected to the connector 15.

The flexible tubing 16 extends to a heat and moisture exchange (HME) device 22 forming a part of the humidifier apparatus 2. The device 22 has an outer housing 23 and an exchange element 24 made of paper or foam plastics treated to be hygroscopic. On the patient side of the exchange element 24, within the housing 23, there is an electrical heater 25 covered by an absorbent wick 26. A water inlet 27 is located close to the wick 26 and is connected via tubing 28 to a water reservoir in the form of a suspended bag 29 of sterile water. The tubing 28 passes through a peristaltic pump 30 contained within the same housing 31 as the control unit 20. The control unit 20 controls the speed of the pump 30 and also provides power output to the heater 25 via a lead 32. Various displays may be provided on the housing 31, such as a display 33 of humidity, as sensed by the sensor 3.

In operation, the ventilator 4 supplies gas to the patient via the HME device 22 and gas supply means comprising the tubing 16, connector 15 and the tracheal tube 1. Exhaled gas flows from the patient towards the ventilator 4 through the exchange element 24 to which it gives up a large part of its heat and moisture. Inhaled gas flows in the opposite direction through the exchange element 24 and, because it is relatively cool and dry, it takes up heat and moisture from the exchange element. The heat and moisture of the inhaled gas, after passing through the exchange element 24 is supplemented by heat from the heater 25 and moisture evaporated from the wick 26.

The level of humidity of gas supplied to the patient may vary for several reasons, such as, increased respiration rate, change in ambient temperature, or change in performance of the exchange element 24 with time. Any such change in humidity is sensed by the sensor 3 and signalled to the control unit 20. A fall in humidity causes the control unit 20 to increase the speed of the peristaltic pump 30 so as to increase the flow of water to the HME device 22; it may also increase the temperature of the heater 25 to increase the rate of evaporation from the wick 26.

Various modifications are possible. For example, the humidity sensor could be mounted in the HME device 22 or on a separate probe that can be inserted in the tracheal tube 1, as desired, through, for example, a suctioning port in an angled coupling.

What I claim is:

1. A medical humidifier system for automatically controlling the humidity of a gas supplied to a patient, said system comprising: a humidifier, said humidifier including a heat and moisture exchange device, a supply of water to the exchange device, and a heater for heating the water supplied to the exchange device; tubing connected at one end with said humidifier; a patient breathing device; a gas connector connected at one end to said patient breathing device and at an opposite end to said tubing such that humidified gas flows to and from said moisture exchange device and to and from a patient via said tubing, said connector and said breathing device; a humidity sensor connected in said connector and exposed to gas flow through the connector for directly sensing the humidity of gas actually being supplied to a patient; and means responsive to an output from said sensor for automatically producing an increase in the humidification of the gas by said humidifier when there is a decrease in the sensed humidity of the gas and a decrease in the humidification of the gas by said humidifier when there is an increase in the sensed humidity of the gas.

2. A medical humidifier system according to claim 1 wherein said humidifier includes a water pump, said humidity sensor being connected to control the speed of said pump.

3. A medical humidifier system according to claim 1 wherein said humidity sensor is connected to control the temperature of said heater.

4. A medical humidifier system for automatically controlling the humidity of a gas supplied to a patient, said system comprising: a humidifier, said humidifier including a heat and moisture exchange device, a supply of water to the exchange device, and a heater for heating the water supplied to the exchange device; a patient breathing device; tubing connected at one end with said humidifier and at its other end with said patient breathing device such that humidified gas flows to and from said heat and moisture exchange device and to and from a patient via said tubing; a humidity sensor located at said breathing device for directly sensing the humidity of gas actually being supplied to a patient; and means responsive to an output from said sensor for automatically controlling humidification of the gas such that a fall in sensed humility produces an increase in humidification of the gas by said humidifier.

5. A medical humidifier system according to claim 4, wherein said humidifier includes a pump for supplying water to said exchange device, the output of said humidity sensor being operative to control the speed of said pump.

6. A medical humidifier system according to claim 5, wherein the output of said humidity sensor is also operative to control the temperature of said heater.

* * * * *